United States Patent
Papiorek

(10) Patent No.: US 9,149,603 B2
(45) Date of Patent: Oct. 6, 2015

(54) PORT CANNULA FOR THE PUNCTURING OF PORT CATHETERS

(71) Applicant: Fresenius Kabi Deutschland GmbH, Bad Homburg (DE)

(72) Inventor: Martina Papiorek, Hünfelden (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 98 days.

(21) Appl. No.: 13/737,152

(22) Filed: Jan. 9, 2013

(65) Prior Publication Data

US 2013/0226103 A1    Aug. 29, 2013

Related U.S. Application Data

(60) Provisional application No. 61/584,387, filed on Jan. 9, 2012.

(30) Foreign Application Priority Data

Jan. 9, 2012   (EP) ..................................... 12150516

(51) Int. Cl.
  *A61M 25/00* (2006.01)
  *A61M 5/32* (2006.01)
  *A61M 39/02* (2006.01)

(52) U.S. Cl.
  CPC ......... *A61M 25/0068* (2013.01); *A61M 5/3286* (2013.01); *A61M 39/0208* (2013.01)

(58) Field of Classification Search
  CPC ..................... A61M 5/3286; A61M 2205/195; A61M 5/158; A61M 2005/1581
  USPC .............. 163/1; 604/170.03, 264, 272, 274; 606/181, 185, 223
  See application file for complete search history.

(56) References Cited

U.S. PATENT DOCUMENTS

| | | | | |
|---|---|---|---|---|
| 5,290,267 | A * | 3/1994 | Zimmermann | 604/272 |
| 5,575,780 | A * | 11/1996 | Saito | 604/272 |
| 5,820,609 | A * | 10/1998 | Saito | 604/272 |
| 6,517,523 | B1* | 2/2003 | Kaneko et al. | 604/272 |
| 6,641,395 | B2* | 11/2003 | Kumar et al. | 433/165 |
| 2002/0072754 | A1* | 6/2002 | Camerlengo | 606/107 |
| 2006/0276759 | A1* | 12/2006 | Kinast et al. | 604/272 |
| 2009/0216259 | A1* | 8/2009 | Sakata et al. | 606/181 |
| 2009/0318946 | A1* | 12/2009 | Tamesada | 606/181 |
| 2012/0289815 | A1* | 11/2012 | Keast et al. | 600/411 |

* cited by examiner

*Primary Examiner* — Nicholas Lucchesi
*Assistant Examiner* — Gerald Landry, II
(74) *Attorney, Agent, or Firm* — Occhiuti & Rohlicek LLP

(57) ABSTRACT

A port cannula for puncturing implantable or implanted port catheters includes a cannula tube with a ground surface, which is formed from a ground cut inclined with respect to a center axis of the cannula tube by a ground-cut angle and from two facet cuts lying at an angle to each other, and of a cannula tip which is provided by the ground surface and which is oriented via a first bend in the direction of the center axis of the cannula tube. The ground cut and the facet cut are adapted to each other in such a way that, on the one hand, during puncturing, a bending of the cannula is least reduced and, on the other hand, the pain caused to the patient is kept within an acceptable range.

27 Claims, 7 Drawing Sheets

Figure 1:
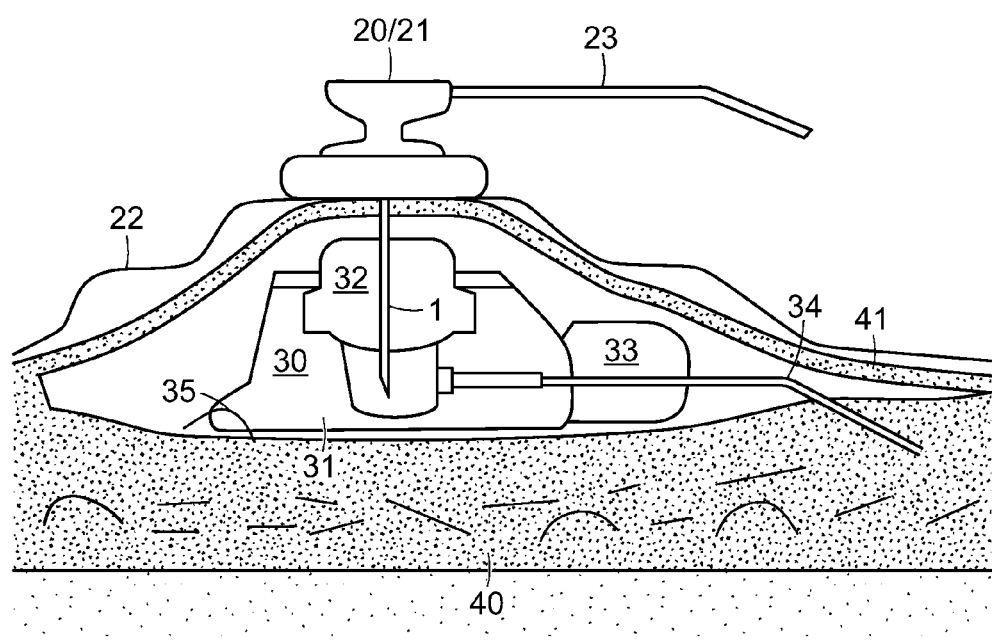

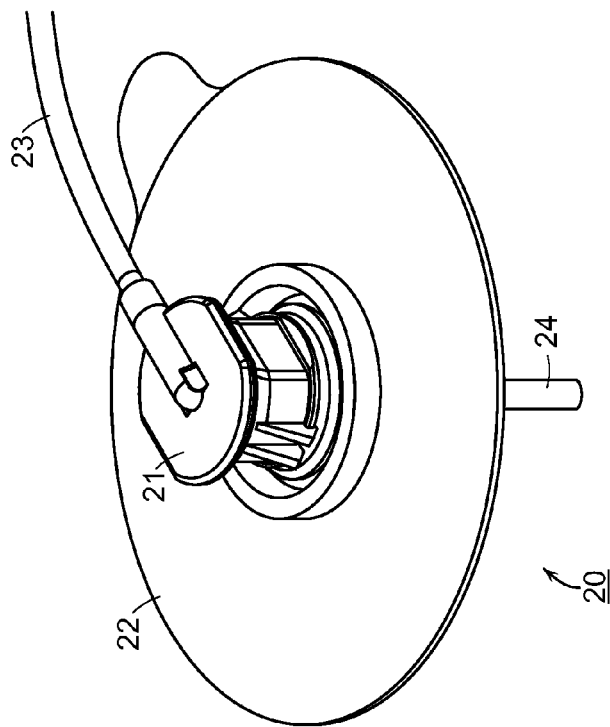
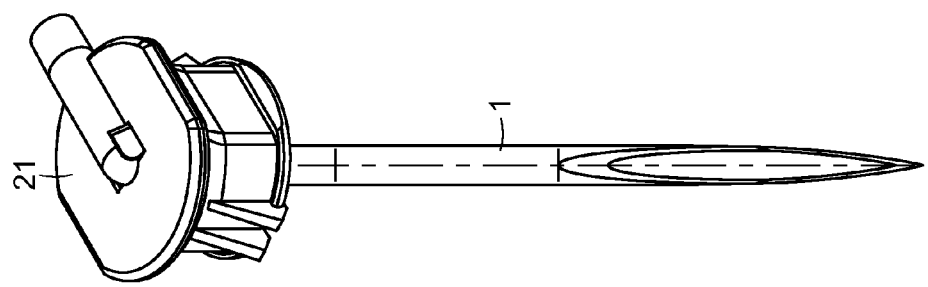
FIG. 6A
FIG. 6B

PORT CANNULA FOR THE PUNCTURING OF PORT CATHETERS

CROSS REFERENCE TO RELATED APPLICATIONS

This application claims priority to European application number 12150516.8, filed Jan. 9, 2012, and U.S. Provisional application No. 61/584,387, filed Jan. 9, 2012. The contents of the aforementioned applications are incorporated herein in their entirety.

DESCRIPTION OF THE INVENTION

The present invention relates to a port cannula for the puncturing of implantable or implanted port catheters.

BACKGROUND OF THE INVENTION

Known cannulas (or puncture cannulas) for puncturing or piercing have a more or less strongly inclined wedge-shaped ground surface at an end portion of the cannula. The rear edge of the wedge-shaped ground surface forms a sharp blade. During the puncturing, a blade of this kind has the effect that constituent parts are punched out from the material that is to be pierced. When puncturing tissue for example, this is undesirable on account of the trauma caused. Moreover, the punching-out effect proves extremely undesirable if cannulas of this kind are used to puncture implantable port catheters. Such port catheters generally consist at least of an implantable capsule which has a hollow space for the removal and/or administration of a liquid such as blood, blood components or a medicament. The capsule is connected to a catheter that opens into a vessel or other treatment site. The wall of the implanted capsule directed toward the skin of the patient is provided in the form of a pierceable elastomer membrane, which is pierced by the cannula through the skin. The penetration of a cannula into the membrane of a port catheter causes leaks, since the rear edge of the ground surface punches elastomer material out of the membrane. This results in the formation of holes, which can no longer automatically close under the restoring force of the membrane material. This has the effect that the implanted capsule begins to leak after just a few piercing procedures. Moreover, punched-out elastomer particles can be carried off into the patient or can block the catheter.

The European patent EP 0 495 214 B1 describes a port cannula which can effectively reduce punching-out. The content of said document is incorporated in full, by reference, into the present application. The cannula described in said document is such that the blade formed by the rear edge is substantially concealed by the cannula tip and in this way can no longer cut. This is achieved principally by the fact that the cannula tube is bent laterally toward the piercing part and, in its further course, is hook-shaped and has a lumen opening ground tangentially into the concave recess of the hook-shaped tube, which lumen opening forms, at its rear edge, a blade that is strongly oriented inward on account of the design of the tube. The demands placed on a port cannula are substantially met by the port cannula described in EP 0 495 214 B1.

GENERAL DESCRIPTION OF THE INVENTION

Against the background outlined above, it is an object of the present invention to make available a cannula for the puncturing of port catheters, wherein the puncturing behavior of the cannula should be further improved.

These objects are achieved by the cannula according to independent claim 1. Advantageous embodiments of the cannula according to the invention are the subject matter of the dependent claims.

The inventors have found that the leakages in the membrane of a port or port catheter can result not only from a punching-out of membrane material upon insertion of the cannula. Rather, the cannula can also pull membrane material with it when being withdrawn. This is caused in particular by the fact that the cannula tip, after penetrating the membrane, can strike the bottom of the port and become bent. This results in the formation of a kind of fish-hook or hook at the cannula tip which, during withdrawal, can as it were "scrape out" material from the membrane. This formation of a hook is promoted in particular by inappropriate use of the cannula, for example if the cannula is inserted into the port catheter with too much force and/or at the wrong angle. Here, a sharp tip proves disadvantageous since it has less stability and can more easily deform into a hook shape. However, a sharp tip proves advantageous since it requires less force to be applied during insertion. The lower the required piercing force, the less pain the puncturing causes the patient.

The invention provides in general that the ground surface of the cannula, in particular the ground cut and the facet cut, are designed and adapted to one another in such a way that, on the one hand, formation of a hook is avoided as far as possible or is at least reduced and, on the other hand, the pain that the patient experiences during the puncturing procedure is maintained within an acceptable range.

The present invention is described in detail on the basis of a cannula for the puncturing of an implantable port. The cannula or port cannula is constructed at least from a cannula tube with a ground surface, which is formed at least from a ground cut inclined with respect to a center axis of the cannula tube by a ground-cut angle ($\beta$) and from two facet cuts lying at an angle ($\gamma$) to each other, and of a cannula tip which is provided by the ground surface and which is oriented via a first bend in the direction of the center axis of the cannula tube, characterised in that the ground-cut angle ($\beta$) lies in a range of $\beta=13°$ to $22°$, preferably $\beta=14°$ to $19°$, particularly preferably $\beta=15°$ to $17°$ and the angle ($\gamma$) between the two facet cuts (12) lies in a range of $\gamma=90°$ to $120°$, particularly $\gamma=100°$ to $115°$, particularly preferably $\gamma=105°$ to $110°$.

The ground cut and the facet cut are adapted to one another in such a way that, on one hand, a deformation of the cannula and therefore a hook formation of the cannula is at least reduced and, on the other hand, the pain for the patient is maintained within an acceptable range.

The cannula tip can in this case also extend beyond the center axis of the cannula tube. The center axis of the cannula tube as reference parameter relates always to the non-curved or straight portion of the cannula. The cannula tip is not provided only by the frontmost point or piercing point of the cannula. Instead, the cannula tip is provided by the area of the ground surface which permits the actual cutting process during penetration through the skin of a patient and through the membrane of a port. In particular, the cannula tip is provided by the area of the cannula at which the facet cuts are arranged. As an alternative the cannula can be constructed at least from a cannula tube with a ground surface, which is formed at least from a ground cut inclined with respect to a center axis of the cannula tube by a ground-cut angle ($\beta$) and from two facet cuts lying at an angle (γ) to each other, and of a cannula tip which is provided by the ground surface and which is oriented via a first bend in the direction of the center axis of the cannula tube, wherein the ground-cut angle (β) lies in a range of β=13° to 22°, preferably β=14° to 19°, particularly preferably β=15° to 17° and/or the angle (γ) between the two facet cuts (12) lies in a range of γ=90° to 120°, particularly γ=100° to 115°, particularly preferably γ=105° to 110°.

In a first embodiment of the invention, the ground cut has a ground-surface area of length a. At least one of the two facet cuts has a length c of c<⅓ a. Preferably, both facet cuts have a length c of c<⅓ a. In this way, the punching-out effect is reduced still further.

In a plan view of the front face of the cannula tube along the center axis of the cannula, a lumen of the cannula tube is at least partially concealed by the cannula tip. Preferably, a rear edge provided by the ground cut is at least partially concealed, in particular completely concealed, by the cannula tip. In this way, the punching-out effect can be reduced still further. In a preferred embodiment, a piercing area or a frontmost area of the cannula tip lies in a range g of 0.5 mm above and 0.2 mm below, preferably 0.2 mm above and 0.1 mm below, the center axis of the cannula tube. Preferably, the cannula tip lies in an area above the center axis of the cannula tube.

In a further embodiment of the invention, the first bend of the cannula tip is provided by a preferably single first bend radius (r). The first bend radius lies in particular in a range of r=5 mm to 10 mm, preferably of 7 mm to 9 mm. The first bend of the cannula tip has a first vertex. Preferably, this first vertex lies at a distance e=3 mm to 5 mm, preferably 3.6 mm to 4 mm, from a piercing area of the cannula tip.

In particular, in order to reduce possible punching-out still further, a portion of the ground cut lying between the two facet cuts is at least partially rounded, preferably completely rounded. In detail, the edges of this portion are rounded. The rounding is achieved by a non-abrasive method. Possible examples of non-abrasive methods are glass bead blasting, dry ice blasting and/or CO2 snow blasting. Preferably, all the edges of the ground surface, with the exception of the facet cut, are rounded.

In a preferred embodiment, the cannula according to the invention has at least a second bend. An end portion of the cannula, at which the ground surface is arranged, is oriented away from the center axis of the cannula tube via a second bend. In particular, the end portion of the cannula, at which the ground surface is arranged, is curved, via the second bend, in a direction that is opposite to the direction of the first bend. Preferably, the directions of the first bend and of the second bend lie at an angle to each other of 160° to 200°, preferably of 175° to 185°, particularly preferably of approximately 180°. The designation of the bends results from the sequence in which the bends are arranged starting from the front or the piercing area of the cannula. A kind of spoon is formed by the first bend and the second bend. Therefore, such a cannula is also designated more simply as cannula with spoon curve. The design of the cannula with spoon formation proves advantageous since the position or orientation of the cannula tip via the first bend in relation to the center axis of the cannula tube is less critical.

One embodiment is such that the second bend of the end portion has a second vertex which lies at a distance f=4 mm to 10 mm, preferably f=6 mm to 10 mm, particularly preferably f=6 mm to 8 mm, from a piercing area of the cannula tip. Preferably, the end portion of the cannula, at which the ground surface is arranged, is arranged at an acute angle (α) to the center axis of the cannula tube. In particular, the acute angle (α) lies in a range of α=1° to 10°, preferably α=4° to 7°.

A further embodiment of the invention is characterized in that at least a portion of an outside of the cannula tube has a roughened surface. The handling of the cannula can be improved in this way. In particular, secure fastening of a feeder (see below) can be permitted in this way. The portion with the roughened surface preferably does not extend completely about the circumference of the cannula tube. In particular, this portion has a roughness Rz that lies in a range of Rz=1 µm to 10 µm, preferably of Rz=5 µm to 10 µm. Preferably, the portion of the outside with the roughened surface is arranged at a distance of approximately 1 mm from a rear side of the cannula tube and/or the portion of the outside with the roughened surface has a length (along the center axis) of approximately 2 mm to 15 mm, preferably of approximately 4.5 mm to 6.0 mm.

The material used for the cannula is a biocompatible material. A preferred material for the cannula is stainless austenitic steel. An example of this is X5CrNi18-10 (material No. 1.4301).

The field of the present invention also encompasses a port cannula system comprising an embodiment of an above-described cannula according to the invention. Moreover, the port cannula system comprises a feeder which is connected to the cannula and permits attachment of a hose of a transfer system. The feeder is in this case preferably arranged on a portion of the cannula tube opposite the end portion. The port cannula system can also have a support piece which is connected to the feeder and is designed to place, in particular secure, the port cannula system on the skin of a patient. An example of the support piece is a kind of plaster. In one embodiment, the feeder is arranged on the portion of the outside of the cannula tube having the roughened surface.

The port systems tested with the cannula according to the invention have also proven to be fully functional after approximately 150 piercing procedures. Since the port systems are implanted, the medical personnel cannot see the port system during puncturing and instead can only feel it by touch. It is therefore not possible to guarantee that the puncturing always takes place at the center of the membrane and/or always takes place vertically. This is also not necessary with the cannula according to the invention.

The present invention is explained in detail on the basis of the following illustrative embodiments. For this purpose, reference is made to the attached drawings. The same reference numbers in the individual drawings designate the same parts.

FIG. 1 shows a schematic view of a subcutaneously implanted port catheter.

Figure 2A:
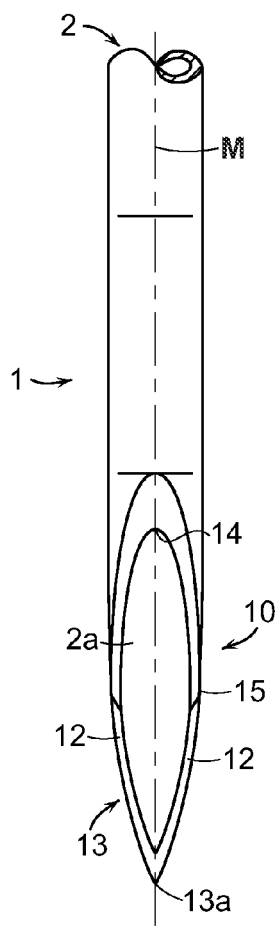
Figure 2B:
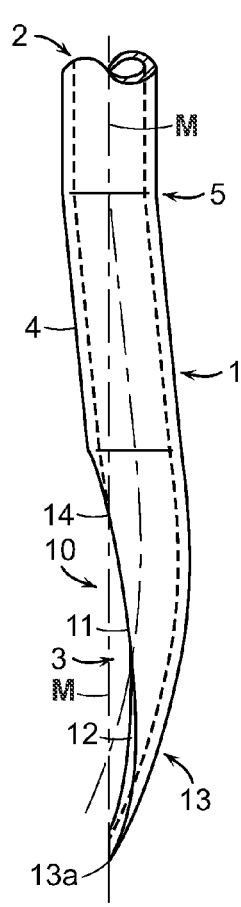
Figure 2C:
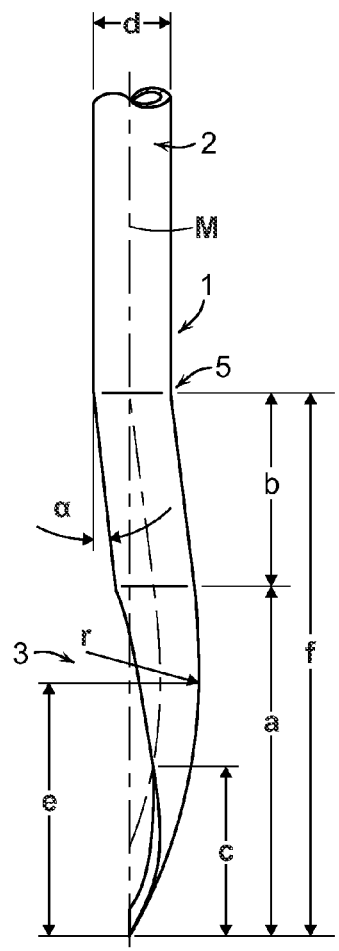

FIGS. 2.a to 2.c illustrate the end portion of a cannula in a plan view of the ground surface (FIG. 2.a) and in a side view without dimensional specifications (FIG. 2.b) and with dimensional specifications (FIG. 2.c).

Figures 1, 3A:
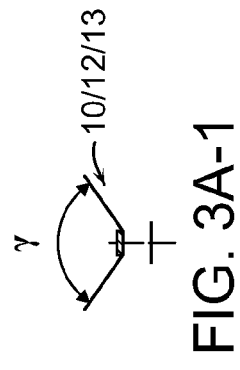
Figure 3A:
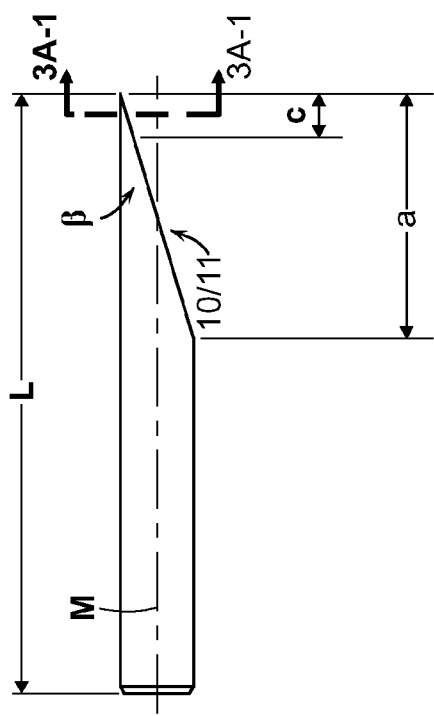
Figure 3B:
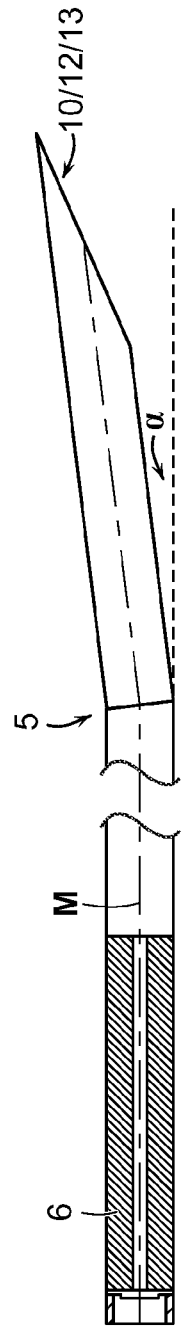
Figure 3C:
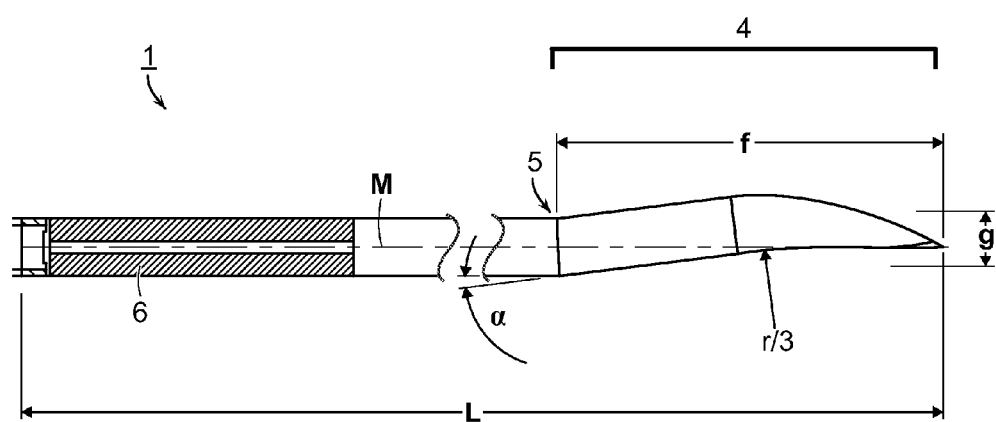

FIGS. 3A to 3C illustrate the steps involved in producing the cannula according to the invention, in a side view. FIG. 3A-1 illustrates a cross sectional view taken along lines 3A-1.

Figure 4A:
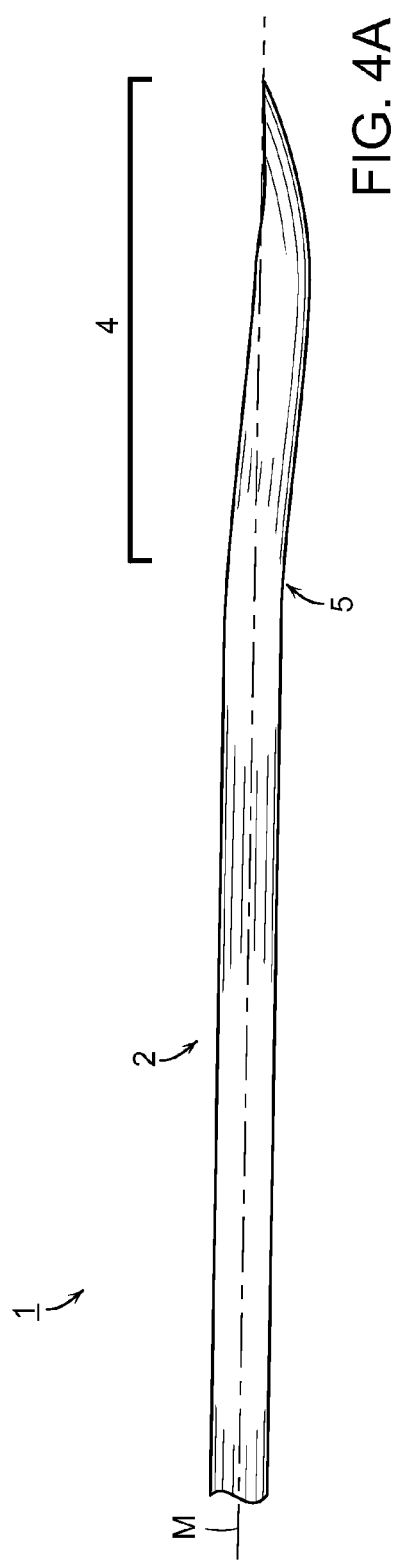
Figure 4B:

FIGS. 4.a and 4.b show a photographic representation of a cannula according to the invention with cannula tube (FIG. 4.a) and without cannula tube (FIG. 4.b).

Figure 5A:
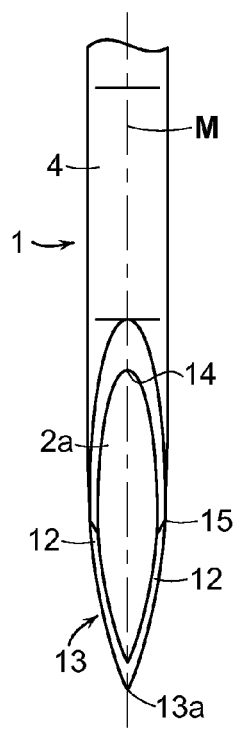
Figure 5B:
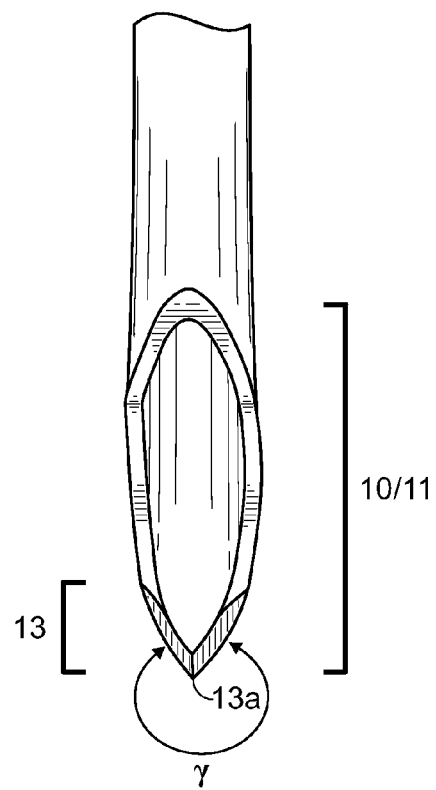

FIGS. 5.a and 5.b show, for comparison, a schematic view (FIG. 5.a) and a photo (FIG. 5.b) of a cannula according to the invention.

FIGS. 6.a and 6.b show a schematic view of a port cannula system without support piece (FIG. 6.a) and with support piece (FIG. 6.b).

FIG. 1 shows an implanted port catheter 30. The port catheter 30 is implanted under the skin 41 and is connected to the surrounding tissue 40 by securing means 35, in order to prevent slippage. The port catheter 30 is formed at least by a housing 31, an elastomer membrane 32 (e.g. of silicone), and a catheter 34 attached to the housing 31 by means of an attachment piece 33. The catheter 34 establishes the connection of the port 30 to the surrounding tissue 41, for example a vein. In order to give a patient a medicament that is to be administered intravenously, for example, the membrane 32 is pierced via the skin 41 by means of a cannula 1 or port cannula 1. The cannula establishes the connection between an infusion chamber formed in the housing 31 to an infusion bag, not shown in the figure. A port catheter 30 can have an approved implantation time of up to 5 years. Accordingly, the port catheter 30 may be punctured often by a port cannula 1. The port membrane 32 must not be damaged to any appreciable extent by the puncturing performed by means of the cannula 1. In order to ensure a permanent operation of a port catheter 30, only special port cannulas 1 can be used. The demands placed on special cannulas of this nature are substantially met by the cannula 1 according to the invention.

FIGS. 2.a to 2.c illustrate the end portion 4 of a cannula 1 in a plan view of the ground surface 10 (FIG. 2.a) and in a side view without dimensional specifications (FIG. 2.b) and with dimensional specifications (FIG. 2.c). FIG. 2.a shows a plan view of the top of the ground surface 10. The rear edge 14 generated by the ground cut 11 can be seen. At least the upper inner area of the rear edge 14 is substantially concealed by the cannula tip 13, in order to avoid as far as possible cutting-out by the rear edge 14. The frontmost area 13a of the cannula tip 13 constitutes the piercing area 13a of the cannula 1. The actual cutting through the skin 41 and through the membrane 32 is effected by the two facet cuts 12. Behind the two facet cuts 12 lies the area 15 of the ground cut 11 which is rounded. All the edges of the ground surface 10 are preferably rounded, with the exception of the facet cuts 12. These are not rounded, since they perform the cutting procedure. The piercing area 13a lies, in this view, on the center axis M of the cannula 1.

Moreover, FIGS. 2.b and 2.c show a side view of the cannula 1 with a partially indicated cross section. For presentation purposes these figures were taken from EP 0 495 214 B1. However, the cannula described in the present patent application has a different design.

The individual features of the cannula 1 are first set forth in FIG. 2.b. The end portion 4, which carries the ground surface 10, is inclined or curved in relation to the cannula tube 2 or to the center axis M of the cannula tube 2 via a second bend 5. The cannula tip 13 is again directed or curved via or through a first bend 3 in the direction of the center axis M of the straight cannula tube 2. The piercing area 13a of the cannula tip 13 lies here on the center axis M of the non-curved cannula tube 2. The piercing area 13a of the cannula tip 13, or the cannula tip 13 as such, can also partially extend in this plane out from the center axis M of the tube 2.

FIG. 2.c now indicates the individual length specifications of the cannula 1. The cannula has a diameter d. The ground cut 11 is characterized by the angle β (see FIG. 3.a). The angle β is independent of the diameter d of the cannula 1. For a 19 G cannula (diameter d=1.1 mm), a cut length a of a=3.2 mm to 4.4 mm, preferably of a=3.6 mm to 4.0 mm, has proven advantageous. For a 20 G cannula (diameter d=0.9 mm), a cut length a of a=2.4 mm to 3.6 mm, preferably of a=2.7 mm to 3.1 mm, has proven advantageous. For a 22 G cannula (diameter d=0.7 mm), a cut length a of a=1.4 mm to 3.0 mm or up to less than 3.0 mm, preferably of a=1.8 mm to 2.4 mm, has proven advantageous. The angle α describes the angle of the second bend 5 of the end portion 4. The area in which the vertex of the second bend 5 (the second vertex) lies is indicated with the arrow tip by reference sign 5. The end portion 4 has a length f. The length f describes the distance between the front point 13a and the second vertex. The radius of curvature r describes the first bend 3 of the cannula top 13. The area in which the vertex of the first bend 3 (the first vertex) lies is indicated with the arrow tip by reference sign 3. The portion of the cannula tip 13 that is curved has a length e. The length e describes the distance between the front point 13a and the first vertex. The length c describes the length of the facet cut 12. In particular, c=0.5 mm to 1.5 mm, preferably 0.8 mm to 1.2 mm. The length b describes the distance between the second vertex 5 and the rear outer edge of the ground cut 11. The span g describes the position tolerance of the piercing area 13a about the center axis M of the cannula tube (see FIG. 3.c). The length of the cannula 1 is dependent on the height of the port 30 and the positional depth of the port 30 in the tissue 40. The cannula can have a length L of L=3 cm to 6 cm.

In order to illustrate the production of the cannula 1 according to the invention, individual method steps are indicated in FIGS. 3.a to 3.c. First, the cannula tube 2 is made available in a straight state. The ground surface 10 should be formed on the end portion 4. The ground surface 10 is here composed of the ground cut 11 and of the two facet cuts 12. For this purpose, in a first step, the ground cut 11 is formed at an angle β. The two facet cuts 12 are then formed at an angle γ (FIG. 3.a). The surface in the portion 6 is preferably roughened before the ground surface 10 is formed.

In a subsequent step, the second bend 5 is first formed. The second bend 5 is made available before the first bend 3. Indeed, the designation of the bends 3 and 5 does not arise from the chronological sequence in which they are produced but instead from the sequence in which the bends 3 and 5 are arranged, starting from the front or the piercing area 13a of the cannula 1.

The end portion 4 is curved via the second bend 5 through an angle α (FIG. 3.b). The end portion 4 is curved away from the center axis M of the cannula tube 2.

In a further step, the now first bend 3 is introduced. For this purpose, the cannula tip 13 is curved in the direction of the center axis M. The cannula tip 13 is provided, at its front end, by a piercing area 13a. By the bending or curvature of the cannula tip 13 in the direction of the center axis M, the rear edge 14 is now substantially concealed. To reduce the punching-out effect still further, the portion 15 that comprises the rear edge 14 is also rounded.

In order to once again demonstrate the structure of the cannula 1, FIGS. 4.a and 4.b show photographs of a cannula 1 according to the invention. These show clearly, on the one hand, the second bend 5 by means of which the end portion 4 of the cannula 1 is curved out from the center axis M of the cannula tube 2. On the other hand, they also show the first bend 3 by means of which the cannula tip 13 is curved back in the direction of the center axis M of the cannula tube 2 in order to conceal the lumen 2a of the cannula tube 2.

After all FIGS. 5.a and 5.b show, for comparison, a schematic view (FIG. 5.a) and a photograph (FIG. 5.b) of a cannula 1 according to the invention and of the end portion 4 thereof. These clearly show the ground cut 11 preferably lying in the short and/or middle area, the shortened facet cut 12 and the greater angle γ of the facet cut 12. The cannula according to the invention substantially reduces in particular a punching-out of membrane material upon insertion of the cannula 1 into the port catheter 30 and also upon withdrawal of the cannula 1 from the port catheter 30.

Finally, FIGS. 6.a and 6.b show a schematic view of a port cannula system 20 without support piece (FIG. 6.a) and with support piece (FIG. 6.b). The feeder 21 is an attachment body for connecting the cannula 1 to a hose 23, for example of a transfer system to an infusion bag (not shown) that contains an active substance to be administered. For this purpose, FIG. 6.b shows an example of a design with a plaster as support piece 22. Moreover, the port cannula system 20 also has a cannula guard 24, for example in the form of a small tube 24. The cannula 1 is arranged in the small tube.

It is obvious to a person skilled in the art that the described embodiments are to be understood as examples. The invention is not limited to these and can instead be varied in many ways without departing from the concept of the invention. Features of individual embodiments, and the features mentioned in the general part of the description, can be combined with one another.

LIST OF REFERENCE SIGNS 1 cannula or port cannula
2 cannula tube
2a lumen of the cannula tube
3 first bend or curvature
4 end portion of the cannula
5 second bend or curvature
6 portion of the cannula tube with roughened surface
10 ground surface
11 ground cut
12 facet cut
13 cannula tip
13a front area or piercing area or piercing point of the cannula tip
14 rear edge of the ground cut
15 area of the ground cut between the facet cuts
20 port cannula system
21 feeder or attachment body
22 support piece or plaster
23 hose
30 port or port system or port catheter
31 port housing or housing
32 port membrane or membrane
33 attachment piece for a catheter
34 catheter
35 securing means for the port
40 tissue
41 skin
M center axis
a length of the ground-surface area or of the ground cut
b distance between start of the ground cut and the second vertex of the second bend
c length of the facet cut
d external diameter of the cannula
e distance between the piercing point of the cannula and the first vertex of the first bend
f length of the end portion or distance between the piercing point of the cannula and the second vertex of the second bend (f=a+b)
g distance of the piercing area from the center axis
r bend radius
α angle of inclination of the second bend
β ground-cut angle
γ angle between the facet cuts
M center axis

The invention claimed is:

1. A cannula for the puncturing of an implantable port, comprising:
a cannula tube with a ground surface, which is formed at least from a ground cut inclined with respect to a center axis (M) of the cannula tube by a ground-cut angle (β) and from two facet cuts lying at an angle (γ) to each other, and of a cannula tip which is provided by the ground surface and which is oriented via a first bend in the direction of the center axis (M) of the cannula tube, wherein the ground-cut angle (β) lies in a range of β=13° to 22°, and the angle (γ) between the two facet cuts lies in a range of γ=90° to 120°,
and wherein the first bend of the cannula tip has a single first bend radius (r), and
wherein the first bend radius (r), lies in a range of r=5 mm to 10 mm.

2. The cannula as claimed in claim 1, wherein the ground cut has a ground-surface area of length a, and at least one of the two facet cuts has a length c of c<⅓ a.

3. The cannula as claimed in claim 1, wherein a lumen of the cannula tube is at least partially concealed by the cannula tip.

4. The cannula as claimed in claim 1, wherein a rear edge provided by the ground cut is at least partially concealed by the cannula tip.

5. The cannula as claimed in claim 1, wherein a piercing area of the cannula tip lies in a range g of 0.5 mm above and 0.2 mm below the center axis (M) of the cannula tube.

6. The cannula as claimed in claim 1, wherein the first bend of the cannula tip has a first vertex, which lies at a distance e=3 mm to 5 mm from a piercing area of the cannula tip.

7. The cannula as claimed in claim 1, wherein a portion of the ground cut lying between the two facet cuts is at least partially rounded.

8. The cannula as claimed in claim 1, wherein an end portion of the cannula, at which the ground surface is arranged, is oriented away from the center axis (M) of the cannula tube via a second bend.

9. The cannula as claimed in claim 8, wherein the end portion of the cannula, at which the ground surface is arranged, is bent, via the second bend, in a direction that is opposite to the direction of the first bend.

10. The cannula as claimed in claim 8, wherein the second bend of the end portion has a second vertex, which lies at a distance f=4 mm to 10 mm from a piercing area of the cannula tip.

11. The cannula as claimed in claim 1, wherein
the end portion of the cannula, at which the ground surface is arranged, is arranged at an acute angle (α) to the center axis (M) of the cannula tube, and
in particular, the acute angle (α) lies in a range of α=1° to 10°.

12. The cannula as claimed in claim 1, wherein at least a portion of an outside of the cannula tube has a roughened surface, which preferably does not extend completely about a circumference of the cannula tube and in particular has a roughness Rz that lies in a range of Rz=1 μm to 10 μm.

13. The cannula as claimed in claim 2, wherein a lumen of the cannula tube is at least partially concealed by the cannula tip.

14. The cannula as claimed in claim 2, wherein a rear edge provided by the ground cut is at least partially concealed by the cannula tip.

15. The cannula as claimed in claim 3, wherein a rear edge provided by the ground cut is at least partially concealed by the cannula tip.

16. The cannula as claimed in claim 2, wherein a piercing area of the cannula tip lies in a range g of 0.5 mm above and 0.2 mm below the center axis (M) of the cannula tube.

17. The cannula as claimed in claim 3, wherein a piercing area of the cannula tip lies in a range g of 0.5 mm above and 0.2 mm below the center axis (M) of the cannula tube.

18. The cannula as claimed in claim 5, wherein a piercing area of the cannula tip lies in a range g of 0.2 mm above and 0.1 mm below the center axis (M) of the cannula tube.

19. The cannula as claimed in claim 1, wherein the first bend radius (r) lies in a range of r=7 mm to 9 mm.

20. The cannula as claimed in claim 6, wherein the first vertex lies at a distance e=3.6 mm to 4 mm-from a piercing area of the cannula tip.

21. The cannula as claimed in claim 7, wherein the portion of the ground cut lying between the two facet cuts is completely rounded.

22. The cannula as claimed in claim 10, wherein the second vertex lies at a distance f=6 mm to 10 mm-from a piercing area of the cannula tip.

23. The cannula as claimed in claim 10, wherein the second vertex lies at a distance f=6 mm to 8 mm from a piercing area of the cannula tip.

24. The cannula as claimed in claim 11, wherein the acute angle ($\alpha$) lies in a range of $\alpha$=4° to 7°.

25. The cannula as claimed in claim 12, wherein the roughness Rz lies in a range of Rz=5 µm to 10 µm.

26. The cannula as claimed in claim 16, wherein the piercing area of the cannula tip lies in a range g of 0.2 mm above and 0.1 mm below-the center axis (M) of the cannula tube.

27. The cannula as claimed in claim 17, wherein a piercing area of the cannula tip lies in a range g of 0.2 mm above and 0.1 mm below-the center axis (M) of the cannula tube.

\* \* \* \* \*